(12) United States Patent
Britton et al.

(10) Patent No.: US 11,083,687 B2
(45) Date of Patent: Aug. 10, 2021

(54) SKIN CARE FORMULATION

(71) Applicant: EMBRYOGENESIS PTY LTD, South Hurstville (AU)

(72) Inventors: Peter Britton, Carlton (AU); Andrew French, Carlton (AU)

(73) Assignee: EMBRYOGENESIS PTY LTD

( * ) Notice: Subject to any disclaimer, the term of this patent is extended or adjusted under 35 U.S.C. 154(b) by 0 days.

(21) Appl. No.: 16/306,361

(22) PCT Filed: Jun. 2, 2017

(86) PCT No.: PCT/AU2017/000124
§ 371 (c)(1),
(2) Date: Nov. 30, 2018

(87) PCT Pub. No.: WO2017/205895
PCT Pub. Date: Dec. 7, 2017

(65) Prior Publication Data
US 2019/0183781 A1   Jun. 20, 2019

Related U.S. Application Data

(60) Provisional application No. 62/369,240, filed on Aug. 1, 2016, provisional application No. 62/345,036, filed on Jun. 3, 2016.

(51) Int. Cl.
| | |
|---|---|
| A61K 8/893 | (2006.01) |
| A61K 9/127 | (2006.01) |
| A61K 8/14 | (2006.01) |
| A61K 8/98 | (2006.01) |
| A61K 35/16 | (2015.01) |
| A61Q 7/00 | (2006.01) |
| A61Q 19/08 | (2006.01) |
| A61K 35/14 | (2015.01) |
| A61K 35/17 | (2015.01) |
| A61K 38/19 | (2006.01) |
| A61K 38/18 | (2006.01) |
| A61K 8/34 | (2006.01) |
| A61K 47/10 | (2017.01) |

(52) U.S. Cl.
CPC ............ *A61K 8/983* (2013.01); *A61K 8/14* (2013.01); *A61K 8/345* (2013.01); *A61K 9/127* (2013.01); *A61K 35/14* (2013.01); *A61K 35/16* (2013.01); *A61K 35/17* (2013.01); *A61K 38/18* (2013.01); *A61K 38/19* (2013.01); *A61K 47/10* (2013.01); *A61Q 7/00* (2013.01); *A61Q 19/08* (2013.01)

(58) Field of Classification Search
CPC .......... A61K 9/983; A61K 8/14; A61K 9/127; A61K 8/983
See application file for complete search history.

(56) References Cited

U.S. PATENT DOCUMENTS

| | | |
|---|---|---|
| 5,631,019 A | 5/1997 | Marx |
| 2007/0081963 A1 | 4/2007 | Oh et al. |
| 2015/0050331 A1 | 2/2015 | Needleman |

FOREIGN PATENT DOCUMENTS

| | | | |
|---|---|---|---|
| WO | WO2013007308 A1 | 1/2013 | |
| WO | WO-2014027363 A1 * | 2/2014 | ......... A61K 38/1841 |
| WO | WO2014126931 A1 | 8/2014 | |

OTHER PUBLICATIONS

Lumen, Platelets, 1 page.*
International Search Report and Written Opinion; dated Jul. 24, 2017 for PCT Application No. PCT/AU2017/000124.

* cited by examiner

*Primary Examiner* — Kyle A Purdy
(74) *Attorney, Agent, or Firm* — Mendelsohn Dunleavy P.C.

(57) ABSTRACT

There is provided a skin care formulation for transdermal administration of a component of a blood product, the formulation comprising a blood product, a transdermal carrier; and a liposomal base, wherein at least a portion of the blood product and transdermal carrier is contained within liposomes of the liposomal base.

1 Claim, No Drawings

SKIN CARE FORMULATION

RELATED APPLICATIONS

This application claims the benefit of U.S. Provisional Patent Application No. 62/345,036, filed on 3 Jun. 2016 and U.S. Provisional Patent Application No. 62/369,240, filed on 1 Aug. 2016 the disclosures of which are hereby expressly incorporated by reference in their entireties.

TECHNICAL FIELD

The technology relates to liposomal skin care formulations comprising blood serum, plasma or components thereof contained within liposomes. In particular, the technology relates to liposomal skin care formulations for systemic application of a component of blood serum or plasma by a transdermal route.

BACKGROUND

Human skin is subject to deterioration due to numerous factors including aging and dermatological disorders conditions or diseases such as dermatitis, psoriasis, eczema, pruritus, acne, rash, dryness and wounding. In addition, deterioration occurs from environmental factors such as from wind, air conditioning, and central heating, or through the normal ageing process, which may be accelerated by exposure of skin to sun. In particular, ageing is characterized by the appearance of wrinkles, variations in skin pigmentation and the loss of elasticity and compactness.

The pathogenesis of skin ageing is characterized by a decrease in collagen synthesis and an increase in collagen breakdown. The loss of dermal collagen is contributes to or facilitates wrinkling.

Alopecia (Hair loss, either complete or partial) affects both men and women but increases in prevalence as age increases. The hair loss process typically involves a process of follicular miniaturization, in which the cells in the hair follicle begin to deteriorate. Consequently, the hair's growth phase is shortened and hair is prevented from maturing into the pigmented terminal hair typically seen on the head. Over time the follicle goes dormant and ceases producing hair completely.

Numerous cosmetic and therapeutic skin care products are currently available for topical use to reduce the effects of skin ageing, skin conditions or hair loss. These typically comprise various chemical components, polymers, oils, antioxidants and the like.

It is believed that biological factors that stimulate collagen production and cell growth in wound healing might provide benefits for ageing skin and hair loss and such factors, including growth factors, peptide fragments, and other biologically active molecules have been incorporated into anti-aging cosmetics and therapeutics.

While the use of biological factors to treat aging skin is gaining favor there remains an unmet need for effective topical formulations for the prevention and treatment of skin damage, wrinkles and other defects associated with aging or caused by environmental factors.

The present inventors have developed a formulation for transdermal delivery of one or more components of a blood product such as plasma or serum.

SUMMARY

In a first aspect, there is provided a skin care formulation for transdermal administration of a component of a blood product, the formulation comprising: a blood product;
a transdermal carrier; and
a liposomal base;
wherein at least a portion of the blood product and transdermal carrier is contained within liposomes of the liposomal base.

The skin care formulation may be present in a nasal dosage form or an oral dosage form for transdermal delivery of the component of the blood product. The oral dosage form may be selected from a sublingual troche, tablet, wafer or lozenge. In some embodiments the oral dosage form is a buccal troche, tablet, wafer, lozenge or orally disintegrating tablet.

In one embodiment the formulation may comprise a therapeutically effective dose of a component of the blood product.

The formulation may additionally comprise an transdermal enhancer.

The blood product may be selected from plasma, serum, platelet rich plasma, conditioned plasma, conditioned serum, and combinations thereof.

In some embodiments the conditioned serum is autologous conditioned serum.

The blood product may be derived from a subject of any age, for example and 18-25 year old, a 25-35 year old, a 35-45 year old, a 45-55 year old, a 55-65 year old or a subject that is 65 or more years old.

The blood product may be derived from a placenta and/or an umbilical cord.

The blood product may be a human blood product. In some embodiments the blood product may be pooled from a number of humans or produced from blood pooled from a number of humans. The blood product may be from an umbilical cord, placenta or donated blood.

In some embodiments the blood product may comprise fragments of regenerative cells. The regenerative cell fragments may be selected from mesenchymal stem cells, endothelial progenitor cells, hematopoietic stem cells, monocytes, macrophages, keratinocytes, and fibroblasts. The skin care formulation may include a blood product comprising fragments of regenerative cells The blood product may be lyophilized.

The component of serum or plasma may be a growth factor, cytokine, chemokine, hormone, vitamin, or cell fragment.

The growth factor may be selected from endothelial growth factor (EGF), hepatocyte growth factor (HGF), basic fibroblast growth factor (bFGF), granulocyte colony-stimulating factor (G-CSF), vascular endothelial growth factor (VEGF), transforming growth factor alpha (TGF-α), TGF-β1, TGF-β2, TGF-β3, platelet-derived growth factor (PDGF)-AA, PDGF-AB, PDGF-BB, insulin-like growth factor-1 (IGF-1), BMP, BDNF, EGF, HGF, PDGF, FGF, PGF, GDF-8, NGF, Epo, TPO, TCGF, IGF-I, IGF-II, KGF, VEGF, and any combination thereof.

The cytokines may be pro-inflammatory or anti-inflammatory.

The pro-inflammatory cytokine may be for example granulocyte macrophage colony-stimulating factor (GM-CSF), interleukin (IL)-1α, IL-1β, IL-2, IL-2R, IL-3, IL-6, IL-7, IL-8, IL-9, IL-10, IL-11, IL-12, IL-12p40/p70, IL-13, IL-14, IL-15, IL-17, tumour necrosis factor (TNF)α, TNF-β, interferon (IFN)-α, INF-β, INF-γ or any combination thereof.

The anti-inflammatory cytokine may be for example IL-1RA, IL-4, IL-5, IL-10, IL-13, IFNα or any combination thereof.

The chemokine may be eotaxin, protein 10 (IP-10), monocyte chemoattractant protein-1 (MCP-1), IFNγ-induced monokine, macrophage inflammatory protein (MIP)-1α, MIP-1β, RANTES or any combination thereof.

The hormone may be selected from an amino acid hormone, eicosanoid hormone, a peptide hormone, and a steroid hormone.

The amino acid hormone may be selected from epinephrine, melatonin, triiodothyronine, and thyroxine.

The eicosanoid hormone may be selected from prostaglandins, leukotrienes, prostacyclin, and thromboxane.

The peptide hormone may be selected from amylin, anti-mullerian hormone, adiponectin, angiotensinogen, angiotensin, vasopressin, atrial natriuretic peptide, brain natriuretic peptide, calcitonin, cholecystokin, corticotropin-releasing hormone, cortistatin, encephalin, endothelin, erythropoietin, galanin, gastric inhibitory peptide, gastrin, ghrelin, glucagon, glucagon-like-peptide-1, Gonadotropin-releasing hormone, Growth hormone-releasing hormone, hepcidin, Human chorionic gonadotropin, Human placental lactogen, human growth hormone, Inhibin, Insulin, Insulin-like growth factor, leptin, lipotropin, melanocyte stimulating hormone, motilin, orexin, oxytocin, pancreatic polypeptide, parathyroid hormone, pituitary adenylate cyclase-activating peptide, prolactin, prolactin releasing hormone, relaxin, renin, secretin, somatostatin, thrombopoietin, thyroid-stimulating hormone, and vasoactive intestinal peptide.

The steroid hormone may be selected from testosterone, dehydroepiandrosterone, androstenedione, dihydrotestosterone, aldosterone, estradiol, estrone, estriol, cortisol, progesterone, calcitriol, and calcidiol.

The liposomal base may be an emulsion that includes a lipophilic component and an aqueous component. The liposomal base may be a lotion, a cream, a gel or a paste. Examples of suitable liposomal bases include PCCA Lipoderm®, Lipoderm ActiveMax™, Anhydrous Lipoderm and Lipoderm High Molecular Weight™ PCCA, Houston, Tex.

One example of a commercially available liposomal base suitable for use in the formulations provided herein includes, but is not limited to, Lipoderm lipophilic liposome cream (a mixture of about 60-80% wt/wt water, with glycerin, C12-15 alkyl benzoate, glyceryl stearate, dimethicone, cetearyl alcohol, cetearyl glucoside, polyacrylamide, cetyl alcohol, magnesium aluminum silicate, xanthan gum, aloe vera (aloe barbadensis), tocopheryl acetate (vitamin E acetate), prunus amygadalus amara (bitter almond) kernel oil, *Vitis vinifera* (Grape) seed extract, *Triticum vulgare* (wheat) germ oil, retinyl palmitate (vitamin A palmitate), ascorbyl palmitate (vitamin C palmitate), Pro-Lipo Multi-emulsion Liposomic System, tetrasodium EDTA, phenoxyethanol, sodium hydroxymethylglycinate. PCCA, Houston, Tex.

The composition in LIPODERM™ lipophilic liposomic cream is particularly suitable when formulated in accordance with the guidance provided herein. For example, the inventors have discovered that surprisingly, to formulate a composition that does not separate, it is important that the blood product be dissolved in a suitable mixed phase emulsion such as LIPODERM™.

The transdermal carrier may be selected from isopropyl alcohol, dipropylene glycol methyl-ether, butylated hydroxytoluene dipropylene glycol monomethyl-ether, 1-methoxy 2-propanol (glysolv PM/Icinol PM), Ethylene glycol monobutylether (butyl glyxolv/butyl icinol), Butyl di glysolv (butyl-icinol), Transcutol, propylene glycol (PG), N-methyl-2 pyrrolidone (NMP), methylene chloride, diethyl ether, ethanol, acetonitrile, ethyl acetate, benzyl alcohol, a combination of natural oil; ethylene glycol, propylene glycol, dimethyl polysiloxane (DMPX), oleic acid, caprylic acid, 1-octanol, ethanol (denatured or anhydrous), liposomal compositions, suitable plant oils, such as Aloe vera derivatives or sesame seed oil or derivatives thereof, acrylic polymers, rubber-based polymers, polysiloxane-based polymers, polyvinylpyrrolidone-based polymers, dimethylsulfoxide (DMSO), dimethylformamide (DMF), lecithin, Transfersomes® (bi-component vesicular aggregates), ethosomes, azone, castor oil derivatives, such as ethoxylated castor oil, jojoba oil derivatives, corn oil derivatives, and emu oil derivatives.

In one embodiment the administration is systemic administration.

The transdermal carrier may be present in the formulation in an amount from about 1% (w/w) to about 50% (w/w). For example the transdermal carrier may be present in the formulation at about 1% (w/w), about 2% (w/w), about 3% (w/w), about 4% (w/w), about 5% (w/w), about 6% (w/w), about 7% (w/w), about 8% (w/w), about 9% (w/w), about 10% (w/w), about 11% (w/w), about 12% (w/w), about 13% (w/w), about 14% (w/w), about 15% (w/w), about 16% (w/w), about 17% (w/w), about 19% (w/w), about 20% (w/w), about 21% (w/w), about 22% (w/w), about 23% (w/w), about 24% (w/w), about 25% (w/w), about 26% (w/w), about 27% (w/w), about 28% (w/w), about 29% (w/w), about 30% (w/w), about 31% (w/w), about 32% (w/w), about 33% (w/w), about 34% (w/w), about 35% (w/w), about 36% (w/w), about 37% (w/w), about 38% (w/w), about 39% (w/w), about 40% (w/w), about 41% (w/w), about 42% (w/w), about 43% (w/w), about 44% (w/w), about 45% (w/w), about 46% (w/w), about 47% (w/w), about 48% (w/w), about 49% (w/w), or about 50% (w/w).

The transdermal enhancer may be present in the formulation in an amount from amount from about 1% (w/w) to about 30% (w/w). For example the transdermal carrier may be present in the formulation at about 1% (w/w), about 2% (w/w), about 3% (w/w), about 4% (w/w), about 5% (w/w), about 6% (w/w), about 7% (w/w), about 8% (w/w), about 9% (w/w), about 10% (w/w), about 11% (w/w), about 12% (w/w), about 13% (w/w), about 14% (w/w), about 15% (w/w), about 16% (w/w), about 17% (w/w), about 19% (w/w), about 20% (w/w), about 21% (w/w), about 22% (w/w), about 23% (w/w), about 24% (w/w), about 25% (w/w), about 26% (w/w), about 27% (w/w), about 28% (w/w), about 29% (w/w) or about 30% (w/w).

In an embodiment the formulation comprises:
1% to 80% (v/w) of the blood product;
1% to 50% (w/w) of the transdermal carrier; and
up to 80% (w/w) of the liposomal base.

For example the blood product can be present in the formulation in an amount from about 1% to about 80% (w/w) or (v/w). For example the blood product can be present in the formulation in an amount of about 1%, about 2%, about 3%, about 4%, about 5%, about 6%, about 7%, about 8%, about 9%, about 10%, about 11%, about 12%, about 13%, about 14%, about 15%, about 16%, about 17%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80%.

The transdermal carrier may be present in the formulation in an amount from about 1% (w/w) to about 50% (w/w). For example the transdermal carrier may be present in the formulation at about 1% (w/w), about 2% (w/w), about 3% (w/w), about 4% (w/w), about 5% (w/w), about 6% (w/w), about 7% (w/w), about 8% (w/w), about 9% (w/w), about 10% (w/w), about 11% (w/w), about 12% (w/w), about 13% (w/w), about 14% (w/w), about 15% (w/w), about 16% (w/w), about 17% (w/w), about 19% (w/w), about 20% (w/w), about 21% (w/w), about 22% (w/w), about 23% (w/w), about 24% (w/w), about 25% (w/w), about 26% (w/w), about 27% (w/w), about 28% (w/w), about 29% (w/w), about 30% (w/w), about 31% (w/w), about 32% (w/w), about 33% (w/w), about 34% (w/w), about 35% (w/w), about 36% (w/w), about 37% (w/w), about 38% (w/w), about 39% (w/w), about 40% (w/w), about 41% (w/w), about 42% (w/w), about 43% (w/w), about 44% (w/w), about 45% (w/w), about 46% (w/w), about 47% (w/w), about 48% (w/w), about 49% (w/w), or about 50% (w/w).

The liposomal base may be present in the formulation in any amount. For example the base may be present in the formulation in an amount of about 1% (w/w), about 2% (w/w), about 3% (w/w), about 4% (w/w), about 5% (w/w), about 6% (w/w), about 7% (w/w), about 8% (w/w), about 9% (w/w) about 10% (w/w), about 11% (w/w), about 12% (w/w), about 13% (w/w), about 14% (w/w), about 15% (w/w), about 16% (w/w), about 17% (w/w), about 19% (w/w), about 20% (w/w), about 21% (w/w), about 22% (w/w), about 23% (w/w), about 24% (w/w), about 25% (w/w), about 26% (w/w), about 27% (w/w), about 28% (w/w), about 29% (w/w), about 30% (w/w), about 31% (w/w), about 32% (w/w), about 33% (w/w), about 34% (w/w), about 35% (w/w), about 36% (w/w), about 37% (w/w), about 38% (w/w), about 39% (w/w), about 40% (w/w), about 41% (w/w), about 42% (w/w), about 43% (w/w), about 44% (w/w), about 45% (w/w), about 46% (w/w), about 47% (w/w), about 48% (w/w), about 49% (w/w), about 50% (w/w), about 51% (w/w), about 52% (w/w), about 53% (w/w), about 54% (w/w), about 55% (w/w), about 56% (w/w), about 50% (w/w), about 58% (w/w), about 59% (w/w), about 60% (w/w), about 61% (w/w), about 62% (w/w), about 63% (w/w), about 64% (w/w), about 65% (w/w), about 66% (w/w), about 67% (w/w), about 68% (w/w), about 69% (w/w), about 70% (w/w), about 71% (w/w), about 72% (w/w), about 73% (w/w), about 74% (w/w), about 75% (w/w), about 76% (w/w), about 77% (w/w), about 78% (w/w), about 79% (w/w), or about 80% (w/w).

In an embodiment the blood product is Human plasma or plasma lysate, Human serum, Human PRP (platelet rich plasma), or Human Autologous conditioned serum; the transdermal carrier is Propylene Glycol; and the Liposomal base is PCCA Lipoderm® q.s.

In a second aspect there is provided a method of treating, preventing or ameliorating a symptom or sign of a skin defect comprising: topically administering to the skin of a subject in need thereof a formulation of the first aspect in an amount sufficient to treat, prevent or ameliorate a symptom or sign of the skin defect.

The formulation may be administered at least once per day. For example the formulation may be administered may be applied daily, twice daily, three times or more than three times daily.

Application of the formula may be continued until the skin defect is resolved or prevented or until at least one symptom or sign of the skin defect is ameliorated. For example the formulation may be applied over a period of one week, two weeks, three weeks, four weeks, five weeks, six weeks, seven weeks, eight weeks, nine weeks, ten weeks, twelve weeks or longer.

The skin defect may be selected from poor skin texture, wrinkles, fine lines, UV induced skin damage, skin aging, dry skin, hair follicle deterioration, alopecia, dermatitis, eczema, rash, pruritus, sun burn, burns, stretch marks, acne scars, and surgical scars.

The treatment may reduce the number of wrinkles or fine lines by about 5%, 10%, 15%, 20%, 25%, 30%, 35%, 40%, 45% or at least about 50% compared to the number of wrinkles or fine lines before treatment.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

DESCRIPTION

The present inventors have developed a topically applied formulation for transdermal delivery of one or more components of a blood product such as blood serum or blood plasma. In some embodiments the component is systemically administered via the transdermal route.

The formulations include three components: a liposomal base, a blood product and a transdermal carrier.

The blood product in the formulation is present in the aqueous and/or lipophilic portions but is also encapsulated in liposomes of the base. The liposomes have a lipophilic membrane surrounding an aqueous interior compartment. The structure of the liposomes may include multilamellar or unilamellar liposomes or unstructured liposomal aggregates and/or combinations of the same. A portion of the blood product is present in the aqueous compartments of the liposome.

The formulations described herein are useful for preventing, reducing and/or eliminating skin defects such as poor skin texture, wrinkles, frown lines, UV induced skin damage, skin ageing, dry skin, hair follicle deterioration, alopecia, dermatitis, eczema, rash, psoriasis pruritus, sun burn, burns, stretch marks, acne scars and surgical scars (wound healing). Accordingly, the formulations may be used as an alternative or in addition to cosmetic surgery, injectable cosmetic treatments such as fillers (Hyaluronic Acid) BOTOX®, silicone or other products.

Skin ageing is a complex process characterized by decreased in collagen synthesis and increased collagen degradation. A number of growth factors stimulate collagen production. In some embodiments the blood products used in the formulations contain growth and/or inflammatory mediators such as, for example, PDGF, IGFs, FGFs, TGFs, EGF, VEGF, HGF, IL-6, G-SCF and KGF as well as extracellular matrix proteins such as type I and type III collagens, fibronectin, terascin, glycosaminoglycans, versican, decorin and other secreted dermal matrix proteins, which may be useful in preventing or repairing skin defects. In addition peptides such as KTTKS and palmitoyl-KTTKS, which promote collagen synthesis, and argireline, a synthetic peptide that inhibits muscle-induced wrinkling of the skin, may also be added to the formulation.

The formulations may include one of more of the following general types of ingredients:

Emollients: for example plant oils, mineral oils, shea butter, cocoa butter, petrolatum, cholesterol, silicones or animal oils (including emu, mink and lanolin). These emollients contribute to softening and smoothing the skin while functioning to assist in moisture retention. In some embodiments, jojoba, squalene and lanolin are used because of their similarity to and are the least comedogenic (pore-clogging).

Humectants: for example sorbitol, glycols, glycerins and sodium PCA. Humectants act to attract water to the skin and are desirable inclusions in the formulations for applications of the formulations to treat/prevent skin damaged by sun and dehydration.

Soothing agents and anti-irritants: for example bisabolol, allantoin, burdock root, aloe, licorice root, glycyrrhetinic acid, green tea and chamomile extract, may be added to the formulations.

Vitamins and antioxidants: for example vitamins A, B group (in particular vitamins B3, B5 and B9), C and E.

Alpha hydroxy acids (AHAs) and beta hydroxy acids (BHAs): these compounds are believed to be useful to clear pores and remove dead skin thereby promoting smoother, moister skin. Examples of useful AHAs formulations include glycolic acid and lactic acid, fruit or citrus acid, and sugarcane extracts. Examples of a useful BHA is salicylic acid. AHA increases sun sensitivity and so formulations containing AHA typically also include physical and/or chemical sunscreen agents.

Antioxidants: Suitable antioxidants include ascorbic acid, sodium sulfite, sodium metabisulfite, sodium bisulfite, sodium thiosulfite, sodium formaldehyde sulfoxylate, isoascorbic acid, thioglycerol, thiosorbitol, thiourea, thioglycolic acid, cysteine hydrochloride, 1,4-diazobicyclo-(2,2,2)-octane, butylated hydroxytoluene (BHT), ascorbyl palmitate, butylated hydroxyanisole, a-tocopherol, phenyl-a-naphthylamine, and mixtures thereof; and Polysaccharides such as glucomannan or guar gum.

In one embodiment the formulation comprises hyaluronic acid (HA) or a salt thereof. The HA or salt thereof may be present in an amount of 0.1% to 10% by weight of the formulation. For example the For example the HA or salt thereof may be present in the formulation at about 0.1% (w/w), about 0.5% (w/w), about 1% (w/w), about 2% (w/w), about 3% (w/w), about 4% (w/w), about 5% (w/w), about 6% (w/w), about 7% (w/w), about 8% (w/w), about 9% (w/w) or about 10% (w/w).

The formulations are topically applied to a subject for example by rubbing, smearing or massaging into an area of skin.

Assays commonly employed by those of skill in the art may be utilized to test the activity of the particular components, thereby ensuring that an acceptable level of biological activity (e.g., a therapeutically effective amount) is retained. Doses of such therapeutic factors are well known to those of skill in the art and may be found in pharmaceutical compendia such as the Physicians' Desk Reference, Medical Economics Data Publishers; Remington's Pharmaceutical Sciences, Mack Publishing Co.; Goodman & Gilman, The Pharmacological Basis Of Therapeutics, McGraw Hill Publ.

The effective doses of any of the components described herein may routinely be determined using techniques well known to those of skill in the art. A "therapeutically effective" dose refers to that amount of the component sufficient to result in amelioration of at least one sign or symptom of skin defect.

The formulations can have a pH of about 6 to about 9, in some embodiments the pH is from 6.0 to 7.0. In other embodiments the pH can be 1, 2, 3, 4, 5, 6, 7, 8, 9, 10, 11, 12, 13, or 14.

In some embodiments the formulations have UVA and UVB absorption properties. In these embodiments, the formulations have a sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The formulation may comprise any UVA and UVB absorbing compound known in the art. For example the formulation may comprise oxybenzone, avobenzone, octisalate, octocrylene, homosalate, octinoxate, zinc oxide titanium dioxide or any combination thereof.

The formulation is applied topically and can be prepared in the form of a hand or body cream, hair shampoo, under eye cream, bath gel or soap, shaving or after shaving lotion. These forms can be prepared using the formulations described herein in conjunction within methods known in the art.

The formulations can provide systemic delivery via a transdermal route of at least one component of the blood product. The component crosses the skin and enters the circulation (for example the blood or lymph) and is distributed substantially throughout the body (i.e. systemically). Accordingly, while the effect of the formulation will be observable at the site of administration (for example a portion of the skin) the effects will also be observable at sites distal to the site of administration due to the systemic delivery of one or more components of the blood product.

Liposomal Base

Any suitable liposomal base known in the art may be used in the formulations provided herein. Typically the liposomal base is an emulsion that includes a lipophilic component and an aqueous component that are emulsified such that the lipophilic component forms liposomes containing a portion of the aqueous component.

The liposomal base may take any form. For example the liposomal base may be a lotion, a cream, a gel or a paste. Preferably the liposomal base is a lotion or a cream.

One example of a commercially available liposomal base suitable for use in the formulations provided herein includes, but is not limited to, LIPODERM™ cream or gel (a mixture of about 60-80% wt/wt water, with glycerin, C12-15 alkyl benzoate, glyceryl stearate, dimethicone, cetearyl alcohol, cetearyl glucoside, polyacrylamide, cetyl alcohol, magnesium aluminum silicate, xanthan gum, aloe vera (aloe barbadensis), tocopheryl acetate (vitamin E acetate), prunus amygadalus amara (bitter almond) kernel oil, *Vitis vinifera* (Grape) seed extract, *Triticum vulgare* (wheat) germ oil, retinyl palmitate (vitamin A palmitate), ascorbyl palmitate (vitamin C palmitate), Pro-Lipo Multi-emulsion Liposomic System, tetrasodium EDTA, phenoxyethanol, sodium hydroxymethylglycinate). PCCA, Houston, Tex.

Other suitable liposomal bases include, but are not limited to, DEMI-GEL™ emulsion (which is a mixture of 4% lecithin isopropyl palmitate containing lecithin soya granular, isopropyl palmitate NF, sorbic acid NF).

Although use of commercially available liposomal bases, gels and diluents is convenient the formulations provided herein may be prepared with any suitable emulsion.

Blood Products

The formulations described herein contain a blood product. Typically the blood product is serum, plasma or platelet rich plasma (plasma lysate, autologous conditioned serum). However any blood product known in the art may be used in the formulations.

The source of the blood product may be umbilical cord blood or blood retrieved from a placenta from a normal or C-section childbirth delivery. Alternatively or in addition the source of the blood for the blood product blood donated to blood banks or from frozen cord blood units stored in public or family cord blood banks. The source of the blood for the blood product may be from the patient's own blood.

The blood product may be pooled from a number of donors. For example blood from individual donors may be typed, cross-matched or both and pooled according to type and or cross-matching characteristics before preparation of a blood product from the pooled samples. The blood may be pooled from adult donors or from umbilical cords or placentas.

The blood product may comprise fragments of regenerative cells or products from regenerative cells. The term regenerative cells refers to any one or combination (in any proportion) of mesenchymal stem cells, progenitor cells, hematopoietic stem and progenitor cells, monocytes, macrophages, keratinocytes, fibroblasts, and any other cell type, excluding embryonic stem cells, that produces or secretes growth factors, hormones, cytokines or regulatory factors. The fragments of regenerative cells or products thereof may naturally be present in the blood product or may be added from an exogenous source (for example from cultured cells). The regenerative cells may be selected from the group consisting of mesenchymal stem cells, endothelial progenitor cells, hematopoietic stem cells, monocytes, macrophages, keratinocytes and fibroblasts. When added from an exogenous source the regenerative cells may be used immediately or after being frozen for a time. In embodiments where regenerative cells are donated they may be used immediately or after being frozen for a time.

In some embodiments the blood product is lyophilised (also known as freeze drying or cryodesiccation) prior to incorporation into the formulation. Lyophilisation can be achieved by any means known in the art and typically includes four steps, pre-treatment, freezing, primary and secondary drying. The pre-treatment step may include concentrating the blood product, the addition of stability enhancers or preservatives or increasing the surface area of the blood product.

In the second step (freezing) the blood product is cooled to below its triple point (the lowest temperature at which the solid and liquid phases coexist) in order to ensure that sublimation occurs in the drying steps. In some embodiments the freezing step includes annealing in which the temperature is reportedly raised and lowered. In other embodiments freezing is done as rapidly as practical to lower the blood product to below its eutectic point quickly to avoid ice crystal formation. Usually, the freezing temperatures are between −30° C. and −80° C.

During primary drying the pressure is lowered and enough heat is supplied to the blood product for the ice to sublime. The amount of heat necessary can be calculated by a skilled person with consideration of the blood products latent heat of sublimation. Pressure on the blood product is controlled through the application of partial vacuum. Application of a vacuum increases the rate of sublimation. In the primary drying phase about 90-95% of the water in the blood product is sublimated.

The secondary drying phase removes unfrozen water from the blood product and is dependent on the blood product's adsorption isotherms. The temperature is raised higher than in the primary drying phase, and can even be above 0° C. in order to break physicochemical interactions between water molecules and frozen material in the blood product. In some embodiments the pressure on the blood product is further decreased to facilitate desorption of water. The residual water content of the blood product is around 1% to 5%, for example 0.5%, 1%, 1.5%, 2.0%, 2.5%, 3.0%, 3.5%, 4.0%, 4.5% or about 5%.

The blood product can be present in a formulation in an amount from about 1% to about 80% (w/w) or (v/w). For example the blood product can be present in a formulation in an amount of about 1%, about 2%, about 3%, about 4%, about 5%, about 6%, about 7%, about 8%, about 9%, about 10%, about 11%, about 12%, about 13%, about 14%, about 15%, about 16%, about 17%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80%.

The blood product may contain one or more components such as metabolites, amino acids, proteins, growth factors, hormones, trace elements, vitamins and minerals.

For example the blood product component may be selected from acetoacetate, acetone, acetylcholine, adenosine triphosphate, adrenocorticotrophic hormone, alanine, albumin, aluminum, aldosterone, amino acids, alpha-aminobutyric acid, d-aminolevulinic acid, ammonia nitrogen, cAMP, androstenedione, androsterone, angiotensin I, angiotensin II, alpha 1-antitrypsin, arginine, arsenic, ascorbic acid (vitamin C), aspartic acid, aspartic acid (in WBCs), bicarbonate, bile acids, bilirubin, biotin (vitamin H), bradykinin, bromide, cadmium, calciferol (vitamin D2), calcitonin (CT), calcium, carbon dioxide, carboxyhemoglobin (as HbCO), carcinoembryonic antigen, beta-carotene, carotenoids, cephalin, ceruloplasmin, cholecalciferol (vitamin D3), cholecystokinin (pancreozymin), cholesterol, choline, chorionic gonadotropin, citric acid, citrulline, coagulation factors (such as fibrinogen, prothrombin, tissue thromboplastin, proaccelerin, proconvertin, antihemophilic factor, christmas factor, stuart factor, plasma thromboplastin antecedent (zymogen form of factor XI), Hageman factor, fibrin-stabilizing factor, fibrin split products, Fletcher factor, Fitzgerald factor and von Willebrand factor), cobalamin (vitamin B12), Cocarboxylase, complement system (including C1q, C1r, C1s, C2, C3, factor B (C3 proactivator), C4 (b1E-globulin), C4 binding protein, C5 (b1F-globulin), C6, C7, C8, C9 and properdin), compound S, copper, corticosteroids, corticosterone, cortisol, c-peptide, c-reactive protein, creatine, creatinine, cysteine, dehydroepiandrosterone (DHEA), DHEA sulfate, DHEA sulfate, 11-deoxycortisol, dihydrotestosterone (DHT), diphosphoglycerate (phosphate), DNA, dopamine, enzymes, epidermal growth factor (EGF), epinephrine, ergothioneine, erythrocytes and fragments thereof, erythropoietin, estradiol (E2), estriol (E3), estrogen, estrone (E1), fat, free fatty acids, fatty acids, ferritin, alpha-1-fetoprotein, flavin adenine dinucleotide, fluoride, folate, folic acid, fructose, furosemide glucuronide, galactose, gastric inhibitory peptide (GIP), gastrin, globulin, alpha-1-globulin, alpha-2-globulin, beta globulin, gamma globulin, glucagon, glucosamine, glucose, glucuronic acid, glutamic acid, glutamine, glutathione, reduced, glycerol, glycine, glycogen, glycoprotein, cgmp, gonadotropin-releasing hormone, guanidine, haptoglobin, hemoglobin, hexosephosphate p, histamine, histidine, beta-hydroxybutyric acid, 17-hydroxycorticosteroids, 17-hydroxyprogesterone, antibodies (including immunoglobulin A, immunoglobulin D, ilmmunoglobulin G, immunoglobulin M and immunoglobulin E), indican, inositol, insulin, insulin-like growth factor, iodine, iron, isoleucine, ketone bodies, alpha-ketonic acids, lactate, lecithin, leptin, leucine, leukocytes and fragments thereof (including neutrophil granulocytes, neutrophils, eosinophil granulocytes, eosinophils, basophil granulocytes, basophils, lymphocytes, monocytes and phagocytes), lipase p, lipids, lipoproteins, lithium, lysine, lysozyme (muramidase), alpha 2-macroglobulin, magnesium, malic acid, manganese, melatonin, methemoglobin, methionine, methyl guanidine, beta-2-microglobulin, MIP-1a, MIP-1b, mucopolysaccharides, mucoproteins, nerve growth factor (NGF), niacin, norepinephrine, nucleotides, ornithine, oxalate, oxytocin, pancreatic polypeptide, pantothenic acid (vitamin B5), para-aminobenzoic acid, parathyroid hormone (PTH), pentose, phenylalanine, phospholipid, phosphatase, phosphorus, phytanic acid, platelets or fragments thereof, platelet-derived growth factor, polysaccharides, potassium, pregnenolone, progesterone, proinsulin, prolactin, proline, prostaglandin, protein, protoporphyrin, prostate specific antigen, pseudoglobulin I, pseudoglobulin ii, purine, pyrimidine nucleotides, pyridoxine (vitamin B6), pyruvic acid, RANTES, relaxin, retinol (vitamin A), riboflavin (vitamin B2), RNA, secretin, serine, serotonin (5-hydroxytryptamine), silicon, sodium, somatotropin (growth hormone), sphingomyelin, succinic acid, sulfates, sulfur, taurine, testosterone, thiamine, thiocyanate, threonine, thyroglobulin (Tg), thyroid hormones, thyrotropin-releasing hormone, thyroxine (FT4), thyroxine-binding prealbumin, thyroxine-binding globulin, tin, alpha-tocopherol (vitamin e), transcortin, transferrin, triglycerides, triiodothyronine, tryptophan, tyrosine, urea, uric acid, valine, vasointestinal peptide (vip), vasopressin, zinc and any combination thereof.

The blood product component may be a growth factor, cytokine, chemokine, hormone, vitamin, or cell fragment.

The growth factor may be selected from the group consisting of endothelial growth factor (EGF), hepatocyte growth factor (HGF), basic fibroblast growth factor (bFGF), granulocyte colony-stimulating factor (G-CSF), vascular endothelial growth factor (VEGF), transforming growth factor alpha (TGF-α), TGF-β1, TGF-β2, TGF-β3, platelet-derived growth factor (PDGF)-AA, PDGF-AB, PDGF-BB, insulin-like growth factor-1 (IGF-1), BMP, BDNF, EGF, HGF, PDGF, FGF, PGF, GDF-8, NGF, Epo, TPO, TCGF, IGF-I, IGF-II, KGF, VEGF, and any combination thereof.

The cytokines may be pro-inflammatory or anti-inflammatory.

The proinflammatory cytokine may be for example granulocyte-macrophage colony-stimulating factor (GM-CSF), interleukin (IL)-1α, IL-1β, IL-2, IL-2R, IL-3, IL-6, IL-7, IL-8, IL-9, IL-10, IL-11, IL-12, IL-12p40/p70, IL-13, IL-14, IL-15, IL-17, tumour necrosis factor (TNF)α, TNF-β, interferon (IFN)-α, INF-β, INF-γ or any combination thereof.

The anti-inflammatory cytokine may be for example IL-1RA, IL-4, IL-5, IL-10, IL-13, IFNα or any combination thereof.

The chemokine may be eotaxin, protein 10 (IP-10), monocyte chemoattractant protein-1 (MCP-1), IFNγ-induced monokine, macrophage inflammatory protein (MIP)-1α, MIP-1β, RANTES or any combination thereof.

The cytokines may be isolated from the blood product.

In some embodiments the cytokines are freeze dried or lyophilised. These methods are well known in the art and are commonly used to preserve the function of temperature sensitive products, such as enzymes and blood products like cytokines.

The hormone may be selected from the group consisting of an amino acid hormone, eicosanoid hormone, a peptide hormone and a steroid hormone.

The amino acid hormone may be selected from the group consisting of epinephrine, melatonin, triiodothyronine and thyroxine.

The eicosanoid hormone may be selected from the group consisting of prostaglandins, leukotrienes, prostacyclin and thromboxane.

The peptide hormone may be selected from the group consisting of amylin, anti-mullerian hormone, adiponectin, angiotensinogen, angiotensin, vasopressin, atrial natriuretic peptide, brain natriuretic peptide, calcitonin, cholecystokin, corticotropin-releasing hormone, cortistatin, encephalin, endothelin, erythropoietin, galanin, gastric inhibitory peptide, gastrin, ghrelin, glucagon, glucagon-like-peptide-1, gonadotropin-releasing hormone, growth hormone-releasing hormone, hepcidin, human chorionic gonadotropin, human placental lactogen, human growth hormone, inhibin, insulin, insulin-like growth factor, leptin, lipotropin, melanocyte stimulating hormone, motilin, orexin, oxytocin, pancreatic polypeptide, parathyroid hormone, pituitary adenylate cyclase-activating peptide, prolactin, prolactin releasing hormone, relaxin, renin, secretin, somatostatin, thrombopoietin, thyroid-stimulating hormone and vasoactive intestinal peptide.

The steroid hormone may be selected from the group consisting of testosterone, dehydroepiandrosterone, androstenedione, dihydrotestosterone, aldosterone, estradiol, estrone, estriol, cortisol, progesterone, calcitriol and calcidiol.

In some embodiments, each component may be present in an amount from about 0.1-1000 pg/ml, about 1-1000 pg/ml, about 50-1000 pg/ml, about 100-1000 pg/ml, about 200-1000 pg/ml, about 300-1000 pg/ml, about 400-1000 pg/ml, about 500-1000 pg/ml, about 600-1000 pg/ml, about 700-1000 pg/ml, about 800-1000 pg/ml, about 900-1000 pg/ml, about 1-100 ng/ml, about 10-100 ng/ml, about 10-100 ng/ml, about 20-100 ng/ml, about 30-100 ng/ml, about 40-100 ng/ml, about 50-100 ng/ml, about 60-100 ng/ml, about 170-100 ng/ml, about 80-100 ng/ml, about 90-100 ng/ml, or at least about 100 ng/ml.

Transdermal Carriers and Enhancers

The formulation comprises a transdermal carrier facilitates passage of the component of the plasma or serum through the skin. Preferably, the transdermal carrier facilitates passage of the component of the plasma or serum through the skin and into the circulation to so that the component is administered systemically.

It is to be understood that any suitable transdermal carrier or solvent which facilitates transdermal absorption of the component may be used. Examples of suitable transdermal carriers include carriers such as isopropyl alcohol, dipropylene glycol methyl-ether, butylated hydroxytoluene dipropylene glycol monomethyl-ether, 1-methoxy 2-propanol (glysolv PM/Icinol PM), Ethylene glycol monobutylether (butyl glyxolv/butyl icinol), Butyl di glysolv (butyl-icinol), Transcutol, propylene glycol (PG), N-methyl-2 pyrrolidone (NMP), methylene chloride, diethyl ether, ethanol, acetonitrile, ethyl acetate, benzyl alcohol, a combination of natural oil; ethylene glycol, propylene glycol, dimethyl polysiloxane (DMPX), oleic acid, caprylic acid, 1-octanol, ethanol (denatured or anhydrous), liposomal compositions, suitable plant oils, such as Aloe vera derivatives or sesame seed oil or derivatives thereof, acrylic polymers, rubber-based polymers, polysiloxane-based polymers, polyvinylpyrrolidone-based polymers, dimethylsulfoxide (DMSO), dimethylformamide (DMF), lecithin, Transfersomes® (IDEA AG). Transfersomes® are artificial vesicles designed to mimic a cell vesicle and deliver component into a cell. The bounding membrane of a Transfersomes® is more flexible than that of a liposome, allowing it to deform and pass through openings in a barrier, such as the skin, whose diameters are much smaller than the average vesicle size. A Transfersome® is a bi-component, most often vesicular, aggregate. The main functional characteristic of the aggregate is the extreme flexibility and permeability of its bilayer-like membrane coating. Its basis is the interdependency of local membrane shape and composition, which makes the bilayer self-regulating and self-optimising. The bilayer is thus capable of stress adaptation, via local and reversible bilayer component demixing.

Additional transdermal carriers include, but are not limited to, ethosomes, azone, castor oil derivatives, such as ethoxylated castor oil, jojoba oil derivatives, corn oil derivatives, emu oil derivatives, or any other suitable transdermal or transcutaneous carrier or carrier composition.

In an embodiment the transdermal carrier is propylene glycol, DMSO, or alcohol.

The transdermal carrier is typically used in an amount of about 1% (w/w) to about 35% (w/w). For example the amount of enhancer used may be about 1% (w/w), or about 2% (w/w), or about 3% (w/w), or about 4% (w/w), or about 5% (w/w), or about 6% (w/w), or about 7% (w/w), or about 8% (w/w), or about 9% (w/w), or about 10% (w/w), or about 11% (w/w), or about 12% (w/w), or about 13% (w/w), or about 14% (w/w), or about 15% (w/w), or about 16% (w/w), or about 17% (w/w), or about 18% (w/w), or about 19% (w/w), or about 20% (w/w), or about 21% (w/w), or about 22% (w/w), or about 23% (w/w), or about 24% (w/w), or about 25% (w/w), or about 26% (w/w), or about 27% (w/w), or about 28% (w/w), or about 29% (w/w), or about 30% (w/w) or about 29% (w/w), or about 30% (w/w), or about 31% (w/w), or about 32% (w/w), or about 33% (w/w), or about 34% (w/w), or about 35% (w/w), or about 36% (w/w), or about 37% (w/w), or about 38% (w/w), or about 39% (w/w), or about 40% (w/w), or about 41% (w/w), or about 42% (w/w), or about 43% (w/w), or about 44% (w/w), or about 45% (w/w), or about 46% (w/w), or about 47% (w/w), or about 48% (w/w), or about 49% (w/w), or about 50% (w/w).

In certain embodiments a transdermal enhancer is incorporated into the formulation. The term "transdermal enhancer" as used herein refers to substances used to increase permeability and/or accelerate the delivery of a component of a blood product through the skin. Enhancers include monohydric alcohols such as ethyl, isopropyl, butyl and benzyl alcohols; or dihydric alcohols such as ethylene glycol, diethylene glycol, or propylene glycol dipropylene glycol and trimethylene glycol; or polyhydric alcohols such as glycerin, sorbitol and polyethylene glycol, which enhance drug solubility; polyethylene glycol ethers of aliphatic alcohols (such as cetyl, lauryl, oleyl and stearyl) including polyoxyethylene-4-lauryl ether, polyoxyethylene-2-oleyl ether and polyoxyethylene-10-oleyl ether; vegetable, animal and fish fats and oils such as cotton seed, corn, safflower, olive and castor oils, squalene, and lanolin; fatty acid esters such as propyl oleate, decyl oleate, isopropyl palmitate, glycol palmitate, glycol laurate, dodecyl myristate, isopropyl myristate and glycol stearate which enhance drug diffusibility; fatty acid alcohols such as oleyl alcohol and its derivatives; fatty acid amides such as oleamide and its derivatives; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide and dimethylformamide; salicylic acid; benzyl nicotinate; or higher molecular weight aliphatic surfactants such as lauryl sulfate salts, esters of sorbitol and sorbitol anhydride such as polysorbate. Other suitable enhancers include oleic and linoleic acids, triacetin, ascorbic acid, panthenol, butylated hydroxytoluene, tocopherol, tocopherol acetate, tocopheryl linoleate.

Other suitable transdermal enhancers include alcohols, amino acids, Azone® Azone-like compounds, so called soft penetration enhancers, sulphoxides, essential oils, fatty acids and fatty acid esters, macrophilic compounds, phospholipids and phospholipid derivatives and 2-pyrolidone derivatives.

In some embodiments enhancers are incorporated into the formulation in an amount typically up to about 30%. For example the amount of enhancer used may be about 0.05% (w/w), or about 0.1% (w/w), or about 0.5% (w/w), or about 1% (w/w), or about 2% (w/w), or about 3% (w/w), or about 4% (w/w), or about 5% (w/w), or about 6% (w/w), or about 7% (w/w), or about 8% (w/w), or about 9% (w/w), or about 10% (w/w), or about 11% (w/w), or about 12% (w/w), or about 13% (w/w), or about 14% (w/w), or about 15% (w/w), or about 16% (w/w), or about 17% (w/w), or about 18% (w/w), or about 19% (w/w), or about 20% (w/w), or about 21% (w/w), or about 22% (w/w), or about 23% (w/w), or about 24% (w/w), or about 25% (w/w), or about 26% (w/w), or about 27% (w/w), or about 28% (w/w), or about 29% (w/w), or about 30% (w/w).

Preparation of the Formulation

In general the formulations are prepared by adding each of the components to the liposomal base and mixing to homogeneity. For example the blood product and transdermal enhancer, and any other optional components such as transdermal enhancers, exogenous cellular extracts, growth factors, hormones, metabolites, or peptides.

In some embodiments the blood product may be concentrated for example by evaporation, ultrafiltration, cross flow filtration or the like before addition to the liposomal base. In other embodiments the blood product may be fractionated for example by chromatography or precipitation of desired components using for example ammonium chloride to select for and/or concentrate desirable components. The concentration process results in an increased concentration of components such as cytokines, growth factors and chemokines in the blood product that forms part of the formulation.

As a result of the concentration the blood products and hence the formulations, comprise supra-physiological levels of the components.

During preparation of the formulation at least a portion of the blood product and the transdermal carrier is incorporated into the liposomes of the liposomal base such that at least some of the liposomes contain at least a portion of the blood product and the transdermal carrier.

In embodiments where the formulations comprise a transdermal enhancer, a portion of the enhancer may also be present inside the liposome.

In some embodiments the skin care formulation for transdermal administration of a component of a blood product comprises a blood product and a transdermal carrier, wherein the skin care formulation is present in an oral dosage form selected from the group consisting on of a sublingual troche, tablet, wafer or lozenge. In some embodiments the dosage form is a buccal troche, tablet, wafer, lozenge or orally disintegrating tablet.

In some embodiments the oral dosage form is solid at room temperature. Preferably the oral dosage form at least partially dissolves at body temperature within the mouth of a user.

The oral dosage form (e.g. sublingual troche) troche can be prepared using any method known in the art. For example the sublingual troche may be prepared by combining low molecular weight polyethylene glycol (for example with molecular weights of 1300 to 1650 g/mol) with gum acacia, citric acid, a sweetener such as stevia extract powder, and a flavoring such as peppermint oil with the blood product. Preferably the blood product is lyophilized. For example the blood product can be freeze dried plasma from typed and/or cross matched donors.

In some embodiments the oral dosage form further comprises a transdermal enhancer.

Methods

The formulations and dosage forms described herein can be used to treat, prevent or ameliorate at least one symptom or sign of a skin defect, for example by facilitation the transdermal delivery of a blood product. The methods typically comprise topical administration of the formulation to at least a portion of the skin of a subject having a skin defect in an amount sufficient to treat, prevent or ameliorate at least one symptom or sign the skin defect. In some embodiments the methods comprise administration of a component of a blood product using an oral dosage form selected from a sublingual troche, tablet, wafer or lozenge. In some embodiments the oral dosage form is a buccal troche, tablet, wafer, lozenge or orally disintegrating tablet.

In other embodiments the formulation is administered to the nasal mucosa for example using a nasal applicator.

There is also provided a method of improving the quality of hair. In this embodiment the method includes the step of topically applying the formulation to an area of skin, for example, on the head, that has thinning hair or where hair is absent. It is believed that the blood products in the formulations contain components that assist in the reversal of hair follicle deterioration and are thereby useful in improving the quality of hair.

The formulations may also include extracts from natural mediums such as placenta extracts, extracts from Wharton's jelly, or amniotic fluids or components extracted from these tissues, or cord blood plasma, cord blood serum or components derived from them.

The formulation is preferably applied more than once. For example the formulation may be applied daily, twice daily, three times or more than three times daily. Application of the formula may be continued until the skin defect is resolved or prevented or until at least one symptom or sign of the skin defect is ameliorated. For example the formulation may be applied over a period of one week, two weeks, three weeks, four weeks, five weeks, six weeks, seven weeks, eight weeks, nine weeks, ten weeks, twelve weeks or longer.

In some embodiments application of the formulation provides positive effects on skin defects and in some cases assists in the repair of the skin defects. Application of the formulation may have a soothing effect.

Application of the formulation may also prevent or reduce scar formation. For example the formulation may interfere with scar forming proteolytic enzymes (such as tryptase and chymase) or stimulate the inhibition of leucocytic elastatse to block mast cell activity.

Formulations for reducing or preventing scar formation may additionally contain hyaluronic acid (HA) or a salt thereof.

Application of the formulation can also enhance the functional capacity of skin, enhance secretion of growth factors in the skin, enhance circulation to enhance skin regeneration, viability and/or elasticity. The formulations may also improve moisture uptake and retention in the skin by protecting against hypertonic and hypotonic stress, desiccation and dehydration, providing a barrier to inhibit tissue and moisture loss, progressively hydrating the different layers of the skin and softening hard tissue.

Application of the formulation may enhance repair and reconstruction of the extracellular matrix and normal skin architecture, mitogenic activity, procollagen production, collagen production.

It is known that Young's modulus of the skin increases linearly with age. Young's modulus (or the elastic modulus) is a measure of stiffness and defines the relationship between stress (force per unit area) and strain (proportional deformation) in a material. Specifically, Young's modulus is the ratio of stress (pressure) to strain (which is dimensionless). Accordingly, Young's modulus has units of pressure, i.e. pascals or $N/m^2$ or $kg \cdot m^{-1} \cdot s^{-2}$). A high Young's modulus indicates that the material is inelastic and a low Young's modulus indicates that the material is elastic. For example rubber has an approximate Young's modulus of 0.01-0.1 MPa and concrete has an approximate Young's modulus of 30 GPa. Human skin has a Young's modulus of between 0.42 MPa and 0.85 MPa.

Young's modulus of skin can be measured by any method known in the art including Optical Coherence Elastography (OCE), mechanical stretching and suction tests.

Application of the formulations described herein results in a reduction of Young's modulus. For example application of the treatment can result in a reduction of the Young's modulus by up to about 50% compared to the skin before treatment. For example the reduction may be about 5%, about 10%, about 15%, about 20%, about 25%, about 30%, about 35%, about 40%, about 45% or about 50%.

Application of the formulation also reduces the number of visible fine lines and wrinkles. For example the number of visible fine lines may be reduced at least 50% compared to the skin before treatment. The reduction may be about 5%, about 10%, about 15%, about 20%, about 25%, about 30%, about 35%, about 40%, about 45% or at least about 50%. Similarly the number of wrinkles may be reduced by at least 50% compared to the skin before treatment. The reduction may be about 5%, about 10%, about 15%, about 20%, about 25%, about 30%, about 35%, about 40%, about 45% or at least 50%.

Skin Defects

The formulation are useful to treat, prevent or ameliorate at least one symptom or sign of a skin defect.

The skin defect may be a scar, a cosmetic skin defect, a traumatic skin defect, a chronic defect, a scar resulting from non-surgical/accidental trauma, a scar resulting from surgical trauma, a scar resulting from a chronic disease state, a scar resulting from topical irritation, depleted collagen levels, depleted elastin levels, depleted adhesive plaques at the dermal/epidermal junction, damage caused by age-related skin deterioration, collagen mis-alignment, scarring, scar formation, stretch marks, keloids, diabetic neuropathies, hardened-cracked skin, hardened cracked heel tissue, fine lines, wrinkles, or skin sagging.

The skin defect may also be poor skin texture, wrinkles, UV induced skin damage, skin aging, dry skin, dermatitis, eczema, rash, pruritus, sun burn, burns, stretch marks, acne scars, surgical scars.

In other embodiments the skin defect may be hair follicle deterioration or alopecia, Kits In one embodiment, a kit is provided including a formulation as described herein; a container; a label; and instructions which provide methods of applying the formulation. The instructions may be a pamphlet, CD, or other computer readable medium. Further, the instructions may provide information about a website which may contain downloadable content.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

In order that the present invention may be more clearly understood, preferred embodiments will be described with reference to the following drawings and examples.

Exemplary Serum Formulation

| | |
|---|---|
| Human serum | 10 ml |
| Propylene Glycol | 10 gm |
| Liposomal base PCCA Lipoderm ® q.s. | 80 gm |

Comparative Example 3—PRP Formulation

Example 2—Serum Formulation

Exemplary Serum Formulation

| | |
|---|---|
| Human serum | 10 ml |
| Propylene Glycol | 10 gm |
| Liposomal base PCCA Lipoderm ® q.s. | 80 gm |

Example 3—PRP Formulation

Exemplary Serum Formulation

| | |
|---|---|
| Human PRP (platelet rich plasma) | 10 ml |
| Propylene Glycol | 10 gm |
| Liposomal base PCCA Lipoderm ® q.s. | 80 gm |

Example 4—ACS Formulation

Exemplary Serum Formulation

| | |
|---|---|
| Human Autologous conditioned serum | 10 ml |
| Propylene Glycol | 10 gm |
| Liposomal base PCCA Lipoderm ® q.s. | 80 gm |

Example 5—Manufacturing Method

Each of the formulations is prepared using the following general procedure

Weigh Lipoderm (gel or cream) in a suitable container.

Transfer blood product (serum, plasma, PRP, ACS etc) under aseptic conditions to the Lidoderm.

Add additives such as hyaluronic acid, vitamins, antioxidants, transdermal carriers or enhancers.

Mix components with gentle agitation.

Seal the container and allow air to diffuse out of the gel.

Fill into appropriate tub or airless container.

Check pH.

Typically the formulation will have a pH from 6.0 to 7.0.

Example 6—Skin Rejuvenation

Subjects of good general health and with visible fine or deep wrinkles in the face, were chosen. Subjects with a history of, or active, skin disease were excluded. Subjects were asked to stop their current regime of skin care products. Make-up and sunscreens were permitted.

Treatment Regimen

The plasma formulation of Example 1 was applied in mornings and evenings to the facial skin for 6 weeks. A treatment group of 5 subjects were asked to document each application of the formulation. A second group was asked to apply a placebo comprising only the lipodermal base (PCCA Lipoderm®) according to the same treatment regimen.

Results

Subjects were evaluated by a visual assessment of skin quality prior to commencement of the treatment and again after the treatment was complete. Compared to the baseline observations all subjects in the treatment group had significant improvement in texture with the skin feeling firmer and more elastic. There was also a reduction in the number of visible fine lines and wrinkles. In comparison all subjects in the placebo group had no change in skin texture or in the number of visible fine lines and wrinkles compared to baseline observations.

The number of visible fine lines were reduced by 30% compared to the skin before treatment. Similarly the number of visible wrinkles were reduced by 30% compared to the skin before treatment.

All subjects liked the way the formulation felt and indicated that they would continue its regular use after the study period.

It will be appreciated by persons skilled in the art that numerous variations and/or modifications may be made to the technology as shown in the specific embodiments without departing from the spirit or scope of technology as broadly described. The present embodiments are, therefore, to be considered in all respects as illustrative and not restrictive.

The invention claimed is:

1. A skin care formulation for transdermal administration of a component of a blood product, the formulation comprising:
- a blood product selected from plasma, serum, conditioned plasma and combinations thereof; a transdermal carrier; and a liposomal base;
- wherein at least a portion of the blood product and transdermal carrier is contained within liposomes of the liposomal base; and
- wherein the liposomal base is a mixture of about 60-80% wt/wt water, glycerin, 02-15 alkyl benzoate, glyceryl stearate, dimethicone, cetearyl alcohol, cetearyl glucoside, polyacrylamide, cetyl alcohol, magnesium aluminum silicate, xanthan gum, aloe vera, tocopheryl acetate, prunus amygadalus amara kernel oil, *Vitis vinifera* seed extract, *Triticum vulgare* germ oil, retinyl palmitate, ascorbyl palmitate, tetrasodium EDTA, phenoxyethanol, and sodium hydroxymethylglycinate.

\* \* \* \* \*